US010117590B2

(12) United States Patent
Barrett et al.

(10) Patent No.: US 10,117,590 B2
(45) Date of Patent: Nov. 6, 2018

(54) TRANSCUTANEOUS MEASUREMENT OF HEMOGLOBIN CHANGES TO CALCULATE ESTIMATED BLOOD VOLUME CHANGE DURING PERITONEAL DIALYSIS

(71) Applicant: Fresenius Medical Care Holdings, Inc., Waltham, MA (US)

(72) Inventors: Louis L. Barrett, West Point, UT (US); David W. Peterson, Clinton, UT (US); Peter Kotanko, New York, NY (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 59 days.

(21) Appl. No.: 15/190,087

(22) Filed: Jun. 22, 2016

(65) Prior Publication Data

US 2016/0367155 A1 Dec. 22, 2016

Related U.S. Application Data

(60) Provisional application No. 62/182,839, filed on Jun. 22, 2015.

(51) Int. Cl.
*A61B 5/02* (2006.01)
*A61B 5/0295* (2006.01)
(Continued)

(52) U.S. Cl.
CPC .......... *A61B 5/0295* (2013.01); *A61B 5/0261* (2013.01); *A61B 5/4848* (2013.01);
(Continued)

(58) Field of Classification Search
CPC ... A61B 5/0295; A61B 5/7246; A61B 5/0261; A61B 5/6824; A61B 5/4848;
(Continued)

(56) References Cited

U.S. PATENT DOCUMENTS 6,117,099 A 9/2000 Steuer et al.
6,181,958 B1 1/2001 Steuer et al.
(Continued)

FOREIGN PATENT DOCUMENTS

WO WO 2012/068416 A1 5/2012

OTHER PUBLICATIONS

International Search Report for co-pending International Application No. PCT/US2016/038816, dated Sep. 7, 2016.

*Primary Examiner* — Rex R Holmes
(74) *Attorney, Agent, or Firm* — Leydig, Voit & Mayer, Ltd.

(57) ABSTRACT

An embodiment of the disclosure provides a method for measuring change in blood volume using a transcutaneous measurement system applied to a patient's skin. The method involves placing a sensor in contact with the skin of a patient, where the sensor includes a light emitter and a photodetector. An intensity of light emanating from the light emitter is set and an initial intensity of light received at the photodetector is determined, where the light received at the photodetector has traveled through the patient's tissue. A later determination is then made of the intensity of the light received at the photodetector. A change in the blood volume is determined based on the intensity of the light emanating from the light emitter, the initial intensity of light received at the photodetector and the final intensity of light received at the photodetector.

19 Claims, 5 Drawing Sheets

(51) Int. Cl.
*A61B 5/026* (2006.01)
*A61B 5/00* (2006.01)
*A61M 1/28* (2006.01)

(52) U.S. Cl.
CPC .......... *A61B 5/6824* (2013.01); *A61B 5/6828* (2013.01); *A61B 5/7246* (2013.01); *A61M 1/28* (2013.01); *A61B 2562/0238* (2013.01); *A61M 2205/3313* (2013.01)

(58) Field of Classification Search
CPC ......... A61B 5/6828; A61B 2562/0238; A61M 1/28; A61M 2205/3313
See application file for complete search history.

(56) References Cited

U.S. PATENT DOCUMENTS

| | | | |
|---|---|---|---|
| 6,210,591 B1 | 4/2001 | Krivitski | |
| 6,725,072 B2 | 4/2004 | Steuer et al. | |
| 6,746,407 B2 | 6/2004 | Steuer et al. | |
| 7,738,935 B1* | 6/2010 | Turcott | A61B 5/0261 600/336 |
| 8,346,332 B2* | 1/2013 | Kuhn | A61B 5/1459 600/323 |
| 2012/0154789 A1* | 6/2012 | Barrett | A61B 5/14535 356/41 |

* cited by examiner

TRANSCUTANEOUS MEASUREMENT OF HEMOGLOBIN CHANGES TO CALCULATE ESTIMATED BLOOD VOLUME CHANGE DURING PERITONEAL DIALYSIS

CROSS-REFERENCE TO RELATED APPLICATIONS

This patent application claims the benefit of U.S. Provisional Application No. 62/182,839, filed Jun. 22, 2015, which is incorporated by reference in its entirety.

BACKGROUND

Systems are known that provide transcutaneous measurement of blood flow rates in vascular accesses of dialysis patients. Such systems are typically relied upon to determine blood flow at access sites to blood vessels. Proper blood flow at the access sites is very important because these sites are limited on a patient. For example, in hemodialysis, typical access sites are located in the arm, leg, or neck of the patient. Needles are placed into the access to facilitate the easy removal of blood on the "arterial" or upstream side of the dialyzer and typically return the purified blood downstream of the first needle placement on the "venous" side. Unfortunately, in many cases, access sites clot or become otherwise compromised over time. This results in decreased blood flow through the access site necessitating either angioplasty or a surgical fix. Sensing a poor access blood flow may help indicate deterioration of the access site, prompting preemptive action on the site to correct the problem with less invasive measures than would likely have been otherwise required.

A sensor used for transcutaneous measurement of blood flow rates typically includes a pad made up of a flexible circuit board loaded with two light emitting diodes (LEDs) and two photodetectors covered with cured silicon. The LEDs and photodetectors are alternately mounted in a straight line with equal spacing between each. This arrangement forms three illuminated "optical zones" in the patient's tissue where light penetrates the skin (i.e., two outer zones separated by a center zone). The depth and diameter of the illumination zones is determined by the spacing of the LED/photodetector pair and the electrical current driving the LED. LEDs radiating light at 800 nm are used because this wavelength of light is absorbed and scattered by hemoglobin (Hb) and is isosbestic with variations in oxygen content.

The outer two "optical zones" of the sensor observe the average Hb content in the normal patient tissue as a result of normal blood diffusion through the skin. The center "optical zone" is positioned over the access site (e.g. a Gortex graft or a natural fistula) where the concentration of Hb is naturally much higher. In essence, the bulk absorption coefficient of the Hb in the access site is referenced to the average of the outer two zone Hb measurements in normal tissue adjacent the access site. Measures from the adjacent normal tissue give a baseline for the blood flow measurement at the access site.

Once the sensor is firmly and correctly positioned, a 30 ml injection of normal saline is shot into a dialysis needle, which is upstream from the sensor pad. As the saline passes under the sensor's center "optical zone," the Hb drops significantly as the red cells in that zone are temporarily diluted by the saline. This dilution is measured through real time measurements of the bulk extinction coefficient changes during the injection event. Fick's Principle is then applied to the data where the volume of the injection is divided by the integration of the Hb change over the time of the injection to produce the flow rate in the vascular access under test. This method of measuring blood flow rate is explained in detail in U.S. Pat. No. 6,746,407 to Steuer et al., entitled "Method of Measuring Transcutaneous Access Blood Flow."

These types of systems are useful for detecting compromised blood flow rates at access sites for procedures such as hemodialysis. But they have not previously provided any measurement of the progression of a dialysis procedure or the effectiveness of such a procedure. For example, during hemodialysis it is useful to monitor the amount of fluid removed from the patient's blood. With dialysis accomplished in clinical settings extracorporeal blood can be measured to determine the percentage change in blood volume using a device such as a Crit-Line® Monitor, which is available from Fresenius Medical Care North America, 920 Winter Street, Waltham, Mass. 02451. However, if the patient is treated with peritoneal dialysis, this type of dialysis is most often done outside of clinical settings, and through use of a different process where solutions wash the toxins out of the peritoneum and no extracorporeal blood is available to analyze.

SUMMARY

An embodiment of the disclosure provides a method for measuring change in blood volume using a transcutaneous measurement system applied to a patient's skin. The method involves placing a sensor in contact with the skin of a patient, where the sensor includes a light emitter and a photodetector. An initial intensity of light emanating from the light emitter is determined along with an initial intensity of light received at the photodetector, where the light received at the photodetector has traveled through the patient's tissue. A later determination is then made of the intensity of the light received at the photodetector. A change in the blood volume is determined based on the initial intensity of the light emanating from the light emitter, the initial intensity of light received at the photodetector and the final intensity of light received at the photodetector. That change is monitored to help determine when a treatment of the patient involving removal of fluid from the blood (e.g., peritoneal dialysis) is complete.

Another embodiment of the disclosure provides a system for measuring change in blood volume. The system includes a sensor with at least one emitter and at least one photodetector placed against a patient's skin. A controller is coupled to the sensor and a power supply is coupled to both the sensor and the controller. The power supply is configured to provide electrical power to the photodetector(s) in the sensor and provide to the controller a first set of signals indicating initial intensities of light emanating from the at least one emitter. The number of signals in the first set of signals matches the number of emitters. The photodetector(s) is configured to provide to the controller a second set of signals indicative of light intensities received at the photodetector(s) due to the first set of signals. A third set of signals provided to the controller are indicative of light intensities received at the photodetector(s) after the second set of signals. The controller is configured to determine a change in blood volume from the first, second and third sets of signals.

BRIEF DESCRIPTION OF THE DRAWINGS

The present invention will be described in even greater detail below based on the exemplary figures and embodiments. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following.

DETAILED DESCRIPTION

Patients with kidney disease may undergo peritoneal dialysis, which is a type of dialysis that uses the patient's peritoneum in the abdomen as a membrane where fluids and dissolved materials are exchanged from the blood. In peritoneal dialysis, fluid is introduced through a catheter to the abdomen and flushed out via a regular schedule. Peritoneal dialysis is an alternative to hemodialysis. Peritoneal dialysis may be undergone at the patient's home while the patient is sleeping, so the patient does not need to attend a clinic or hospital to undergo dialysis. Since a patient can undergo the procedure at home, work, etc., the patient may not have access to expensive equipment to determine how much fluid is being removed from the body during the dialysis process. Embodiments of the disclosure provide a transcutaneous measurement system to determine change in a patient's blood volume. Although the example environment provided here is with respect to peritoneal dialysis, the transcutaneous measurement may be utilized with any type of dialysis or medical procedure where the change in blood volume of a patient provides pertinent information.

When a patient's kidneys are not working properly, blood volume of a patient may increase. The increase in blood volume presents various risks, for example, increased swelling in legs and arms. Additionally, fluid may enter the abdomen and air spaces in the lungs, and ultimately leading to congestive heart failure. On the other hand, when undergoing dialysis to remove excess fluids and toxins from the body, decrease in blood volume beyond a patient's dry weight may pose great risks. Removing too much fluid may increase heart rate and respiratory rate and/or lower blood pressure to abnormal levels, making the patient lethargic and in extreme cases causing the patient to enter a coma. As such, embodiments of the disclosure provide a method and system for determining change in blood volume and avoid removing or accumulating too much fluid.

Figure 1:
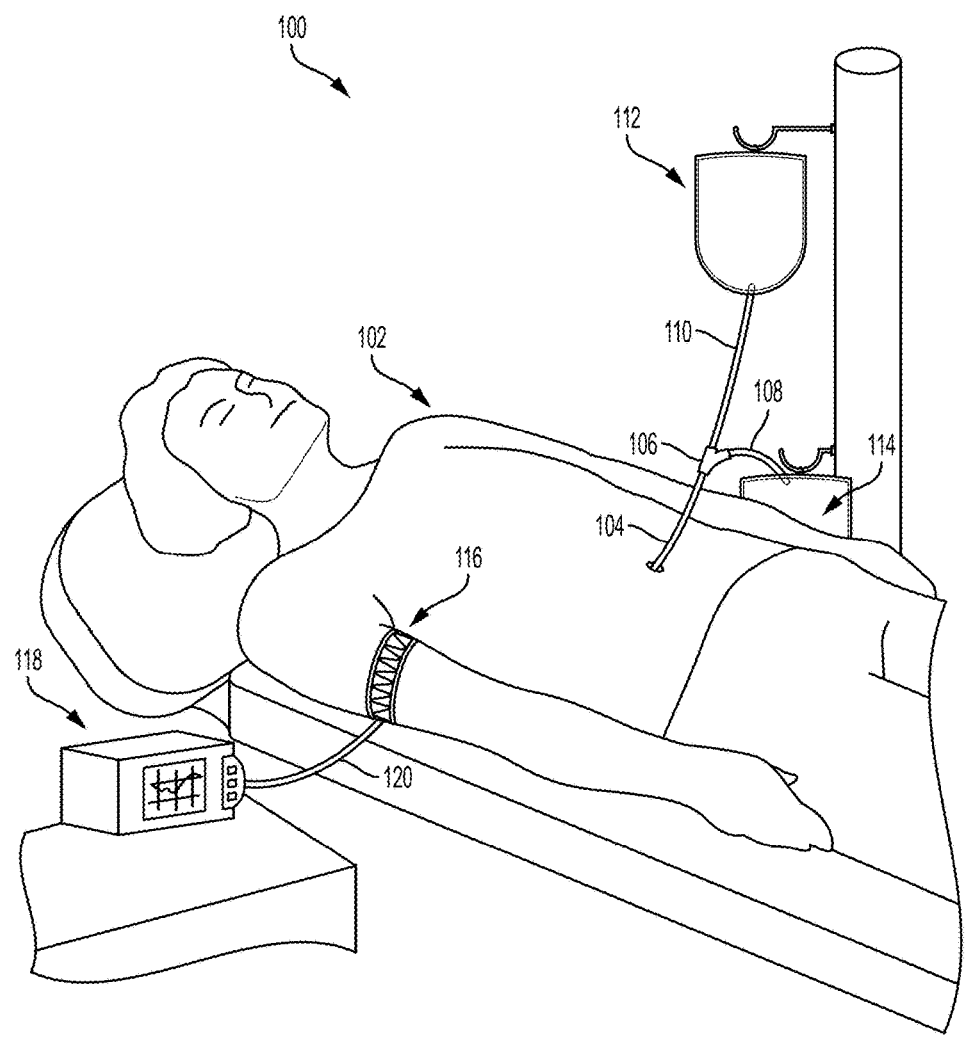
FIG. 1 provides an example environment to apply some embodiments of the disclosure.

FIG. 1 provides an example environment 100 with a patient 102 undergoing peritoneal dialysis and using an embodiment of the disclosure to monitor blood volume change. The patient 102 has a surgically implanted catheter 104 that may connect to other catheters. In FIG. 1, catheter 104 is connected to catheters 110 and 108 through a tube connector 106. Dialysis fluid 112 is introduced to the patient through catheter 110, and waste fluid 114 is extracted from the patient 102 through catheter 108.

In the illustrated embodiment, the patient 102 has a blood volume sensor 116 wrapped around his upper arm. However, the blood volume sensor 116 may be placed anywhere on the body. In some cases, the sensor 116 is placed near the heart because the heart houses fairly large arteries. Because the sensor 116 is sensing blood as blood is diffused to skin, the closer the sensor 116 is to the heart, the shorter the delay between measured fluid level change in tissue and actual fluid level in the circulatory system.

The sensor 116 is electrically connected to an electronic measurement system 118 through a wired connection 120. Examples of the electronic measurement system 118 may be the Crit-Line® Monitor, a graphical display, a desktop computer, a laptop computer, a mobile phone device, etc. In one embodiment, the electronic measurement system 118 not only receives measurement signals from the sensor 116, but also provides power to the sensor through the wired connection 120. The connection between the electronic measurement system 118 and the sensor 116 may be of any conventional type and in one embodiment is a USB connection, providing the capability for both power and data transfer. The sensor 116 includes electronics on a flexible circuit board for facilitating communication with the electronic measurement system 118 as well as electronics for obtaining the measured data related to the change in blood volume.

Figure 2:
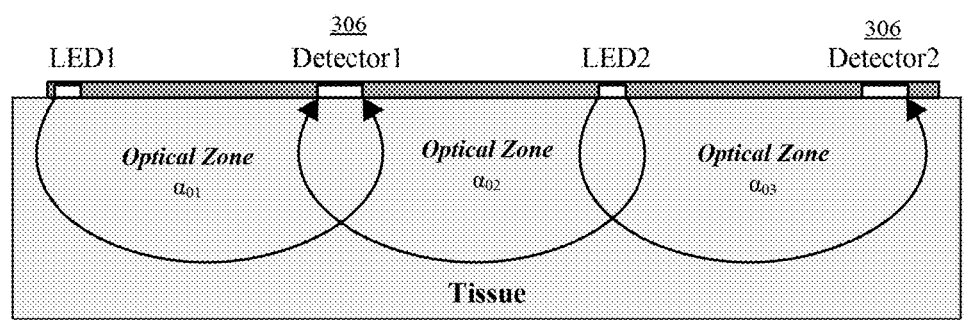
FIG. 2 shows an example design of a sensor pad according to some embodiments of the disclosure.

Embodiments of sensor 116 "optical zones" of human tissue illuminated by one or more emitters is shown in FIG. 2. The "optical zones" of the sensor 116 measure the level of Hb contained in the blood capillaries within the illuminated tissue. The measurement of the level of Hb diffused in the tissue is accomplished by measuring a bulk extinction coefficient of the Hb in the tissue. The "optical zones" define a fixed volume of illumination that is also fixed in its geometry.

In the embodiment illustrated in FIG. 2, three independent measurements from the sensor 116 are made from the three separate "optical zones" and then averaged to obtain the relative tissue Hb content of the tissue within the zones. From this average, traditional relative percent of blood volume change calculations can be achieved. In some embodiments, the transcutaneous device (i.e., sensor and its measurement system) is operated simultaneously with a Crit-Line® Monitor on a normal in-clinic dialysis patient. The blood volume (BV) changes measured by both the transcutaneous device and the Crit-Line® Monitor are recorded in a memory and compared. Theoretically, BV changes from the device and the Monitor should be the same in amplitude, but there will likely be a time dilation effect in the comparison due to the delay in Hb changing in the tissue as measured by the transcutaneous device.

FIG. 2 shows an example design of the sensor 116. The figure also shows the concept of how the "optical zones" illuminate and read the bulk extinction coefficient ($\alpha$) for the tissue within each zone of illumination. FIG. 2 illustrates the sensor 116 as a linear pad for ease of explanation, but other shapes and geometries are possible and probable. For example, the sensor 116 is a cylindrical shape in FIG. 1 in order to form a cuff-shaped design when wrapped around the upper arm of the patient 102. The sensor pad 116 as illustrated in FIG. 2 is shown with three independent "optical zones" measuring the bulk extinction coefficients, $\alpha$, for each zone. These changes in $\alpha$ allow for measurement of tissue Hb and provide for calculation of related relative blood volume changes due to dialysis. For example, in this case, the results of providing three zones allows for averaging that yields improved accuracy. In this situation, each "optical zone" is measured separately and independently of each other, so LED1 and LED2 are not turned ON at the same time. In other implementations, the sensor 116 may comprise a single "optical zone," which may be sufficient for the measurement. In yet another embodiment, the sensor 116 employs geometries other than the linear geometry of the sensor illustrated in FIG. 2. In some embodiments, the two LEDs emit light at a selected isosbestic wavelength between about 800 nm and 830 nm, where light is absorbed and scattered by Hb and is unaffected by variations in oxygen content. In some embodiments, the photodetectors and the LEDs may be spaced about 17 mm apart. The spacing (d) between the LEDs and photodetectors is a function of the light intensity of the LEDs that can be generated and the light sensitivity of the photodetectors, and is a factor in determining the volume of the "optical zone" illuminated. At a constant light intensity, a larger spacing (d) causes light from the LED to travel a longer distance to reach the photodetector, thus, a lower amplitude signal will reach the photodetectors after the light traverses human tissue. If the light intensity cannot be increased to compensate, for a given light intensity there is a limit to how much the spacing between the LEDs and the photodetectors may be increased and still receive a useable signal. This limit is realized when the spacing (d) at a specific light intensity renders the signal received at the photodetector indistinguishable from noise.

Figure 3:
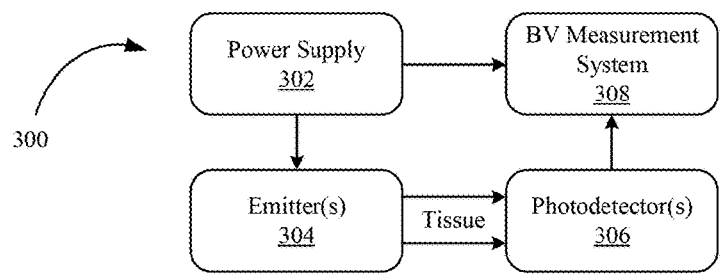
FIG. 3 is a system architecture showing functional units that determines change in blood volume according to some embodiments of the disclosure.

A system architecture 300 of the sensor 116 and the electronic measurement system 118 is illustrated in FIG. 3 to show the functional units of the system. The system architecture 300 includes a power supply 302, one or more emitters 304, one or more photodetectors 306, and a blood volume or BV measurement system 308. The power supply 302 provides power to the emitter 304. The singular form is used for "emitter" and "photodetector" to enhance clarity in explanation, but the illustrated emitter 304 may represent a plurality of emitters, and the illustrated photodetector 306 may represent a plurality of photodetectors. The power supply 302 includes a controller to manipulate or manage the amount of voltage and/or current provided to the emitter 304. The power supply 302 can be realized as one or more batteries, the AC mains and a voltage regulator and/or a current source and other similar sources of power. In the illustrated embodiment, the power supply 302 also provides power to the BV measurement system 308.

The emitter 304 includes one or more emitters, for example, one or more LEDs. In the example sensor 116 illustrated in FIG. 2, there are two LEDs in the emitter 304. The photodetector 306 includes one or more photodetectors that can be, for example, one or more photodiodes. In the example sensor pad provided in FIG. 2, there are two detectors designated as Detector1 and Detector2.

The BV measurement system 308 includes a processor, a controller, or a microcontroller and other circuit components that determine the percent change of blood volume. BV measurement system 308 may include amplifier(s) to increase electrical signal(s) generated by the photodetector 306 in response to light received at the photodetector 306. For example, the electrical signal(s) received from the Photodetector 306 are indicative of the light intensity received at a detector. The BV measurement system 308 may also receive an electrical signal from power supply 302 indicative of light intensity transmitted into tissue by the emitter 304. For example, an LED's light intensity may depend on the magnitude of current flowing through the LED, thus, this current magnitude is provided to the BV measurement system 308 by the power supply 302. The power supply 302 may also provide power to the BV measurement system 308 in order to support and realize functions attributed to the BV measurement system 308. Thus, the BV measurement system 308 utilizes signals indicative of light intensities provided by the emitter 304 and signals indicative of light intensities received by a the photodetector 306 to determine change in blood volume.

Figure 3A:
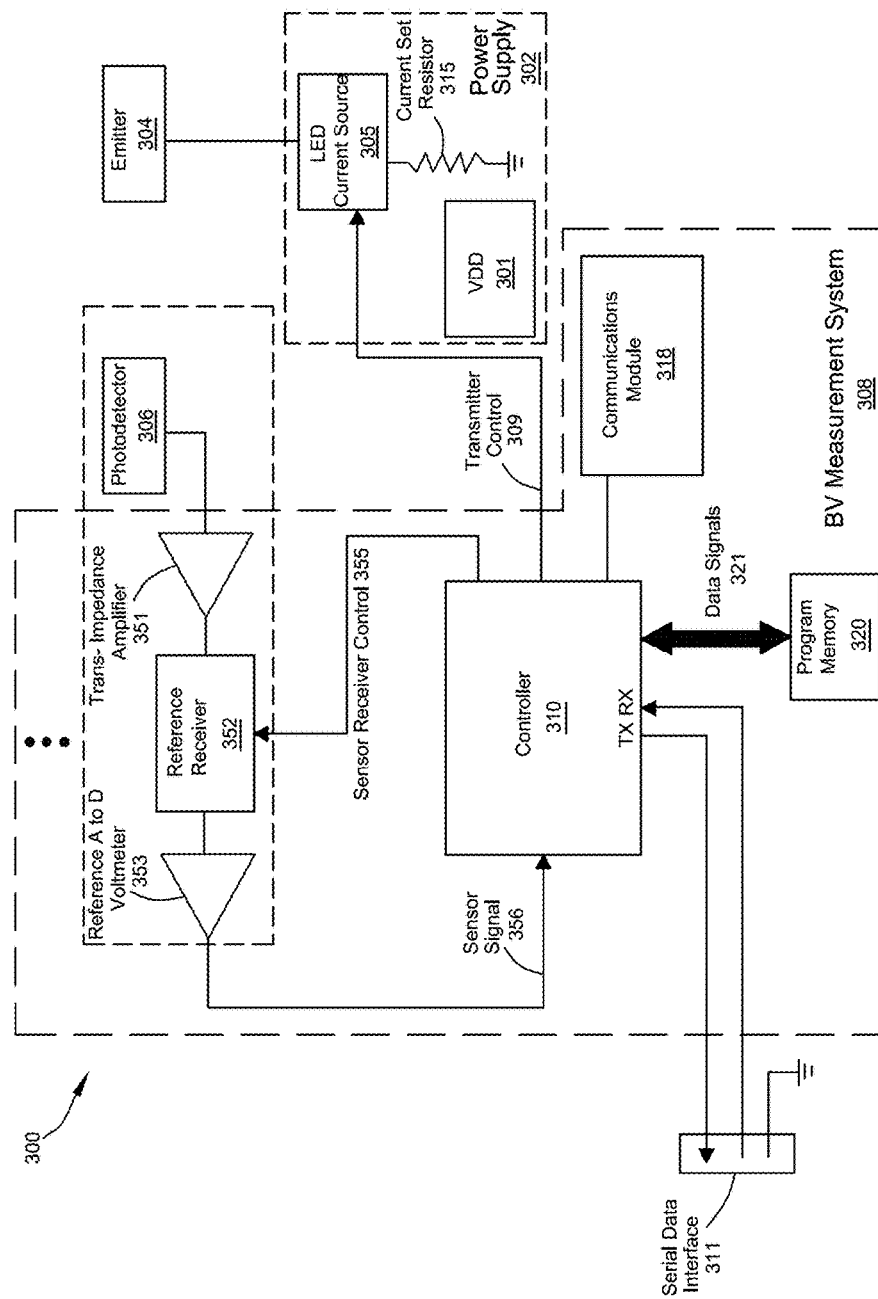
FIG. 3A is a more detailed diagram of the system architecture of FIG. 3.

FIG. 3A schematically illustrates an example embodiment of the sensor 116 and the electronic measurement system 118, which includes the power supply 302 and the BV measurement system 308. FIG. 3A is different from the representation of FIG. 1 in that FIG. 3A is shown to be a compact representation of the sensor 116, electronic measurement system 118, and the wired connection 120. The compact representation can connect to a more elaborate device for display through serial data interface 311. The electronic measurement system 118 includes a controller 310. The controller 310 synchronizes and controls the sensor 116 and the electronic measurement system 118 as a whole. Measurements of the light reaching the photodetector 306 are processed by signal processing hardware (identified as trans-impedance amplifier 351, reference receiver 352, and reference A to D voltmeter 353) and fed to the controller 310. The photodetector 306 is a Silicon photodiode, or an array of Silicon photodiodes or any other photo detector that is sensitive to a selected isosbestic wavelength where light is scattered and absorbed by Hb and yet unaffected by oxygen variation. Suitable photodetectors are available from Hamamatsu Photonics K.K., Hamamatsu City, Japan.

FIG. 3A shows that if multiple photodetectors interface with BV measurement system 308, then the signal processing hardware may be repeated for each photodetector. That is each photodetector 306 will have its own trans-impedance amplifier 351, reference receiver 352, and reference A to D voltmeter 353. In other embodiments, since the change in blood volume is measured consecutively for each "optical zone" and not simultaneously, one trans-impedance amplifier 351, reference receiver 352, and reference A to D voltmeter 353 may be shared by multiple photodetectors, where only one photodetector is connected to the signal processing hardware at a time.

The emitter 304 includes a light-emitting-diode (LED) or an array of LEDs. The emitter 304 may include other light sources, such as LASER emitters, fluorescent light sources, incandescent light sources and the like. Suitable emitters are available from Hamamatsu Photonics K.K., Hamamatsu City, Japan.

In the illustrated embodiment of FIG. 3A, the light amplitude intensity for the LED emitter 304 is controlled by an LED current source 305 with the intensity set by the current set resistor 315. VDD 301 is a voltage supply to power the circuitry for the LED current source 305 and the functional blocks of the BV measurement system 308 as shown in FIG. 3A.

In response to the light reaching it after passing through the tissue defined by the "optical zones," the photodetector 306 generates in a conventional manner a current signal proportional to the intensity of the light it receives and sends the current signal to signal processing circuitry to be processed for use by the controller 310. For example, in the illustrated embodiment in FIG. 3A, a trans-impedance amplifier 351 receives the current signal and amplifies it as necessary and converts the signal to a voltage signal. The voltage signal is then applied to a sensor receiver 352 where it is filtered and conditioned for passing on to an analog-todigital (A to D) voltmeter 353. This voltmeter 353 converts the measured voltage proportional to the light received at the photodetector 306 to a final digital sensor signal 356 formatted to be an input to the controller 310.

The controller 310 in the embodiment illustrated in FIG. 3A also has the option to adjust the amplitude of the light at the LED emitter 304 by adjusting the LED current source 305 to provide more power to the LED emitter 304. A transmitter control 309 signal from the controller 310 to the LED current source 305 accomplishes this task.

The controller 310 may include various components, such as a processor, non-transitory computer readable medium for storing computer code/programs to perform measurement method and/or calibration methods provided throughout in this disclosure, as well as user interface devices, such as keyboard, mouse, touchpad, displays, speakers and the like. For example, in the embodiment illustrated in FIG. 3A, program memory 320 is a non-transitory computer readable medium. Serial interface 311 in FIG. 3A is an example of a communications interface for the controller 310. It passes the blood volume data developed by the BV measurement system 308 to the outside world for display and further analysis. Such a data port can be any of a variety of known formats and interfaces, including RS-232, Universal Serial Bus (USB) and the like.

In the embodiment illustrated in FIG. 1, the electronic measurement system 118 is shown separately connected to the sensor 116 via cable 120. The electronic measurement system 118 is shown to be elaborate, providing an avenue where the data from sensor 116 is used to generate a graphical display of blood volume change information useful to the patient or clinician. An example of a suitable display, for example, is the display of the Crit-Line® Monitor. FIG. 3A provides an alternative where signal processing of the blood volume data may be prepared and stored in program memory 320 before sending out to a display through serial data interface 311.

As an alternative or in addition to the cable 120 in FIG. 1 for communicating data, the controller 310 is coupled to a communication module 318 that enables the transmitting and/or receiving of data and/or other information that may be controlled or used by the controller 310 and/or stored on the memory 320. In an embodiment, the communication module 318 includes a wireless transceiver that wirelessly transmits or receives the data or other information. In an example, the wireless transceiver enables wireless communication between electronic measurement system 118 and peripheral devices that can record or otherwise use data or other information concerning the dialysis treatment. As a further alternative, the electronic measurement system 118 may connect to peripheral devices through an internet connection.

By connecting to peripheral devices, for example, a patient's smartphone, the blood volume data generated by the electronic measurement system 118 may be sent to a remote server in a hospital, clinic, doctor's smart tablet or wherever there is wireless access for real-time monitoring of patient fluid levels during peritoneal dialysis. In this manner, a clinical employee may monitor multiple remote patients at a time without the need of visiting each patient to check in on the progress of dialysis. This remote monitoring improves safety since currently, peritoneal dialysis performed offsite is not monitored but follows a regimented schedule.

In an embodiment, the communication module 318 includes components for short-range wireless communications between the blood monitoring system 14 and the dialysis treatment system 12 via known short-range wireless technology protocol such as, for example, a Bluetooth protocol or an RFID protocol—e.g., a near field communication (NFC) protocol. In other embodiments, wireless communication to and from the blood monitoring system 12 may be facilitated using other wireless technologies, such as via WiFi and/or via an implementation utilizing telecommunication networks.

In connection with the transmission, either via cable 37 or via wireless transmission, the data may be secured and/or encrypted via the controller 310 using appropriate security and encryption protocols according to applicable laws and regulations governing transmission of sensitive data and/or protected medical information.

The geometry and size of the "optical zones" into the skin and underlying tissue are governed by the spacing of the emitter 304 to detector 306 and by the current through the emitter. Photo flux from the emitter 304 is proportional to the current through the emitter, provided the temperature of the emitter remains constant. The temperature of the emitter is mitigated over the measurement period by the emitter (e.g., LED and/or LED array) being against the skin of the patient. Depending on the emitter current, the body can be warmer than the emitter at first, but after a while will reach equilibrium with the body. The body is typically at around 37° C. or 98.6° F.

Once the emitter 306 is in place, it produces a "glow ball" or the "optical zone" into the skin and tissue as shown in FIG. 2. With the sensor pad 116 firmly in place on the patient's observation site (e.g., the upper arm of the patient as illustrated in FIG. 1), then the volume of tissue and skin illuminated is fixed and considered constant. Within the glow ball or "optical zone," there is a component volume of blood. Because the vascular system does not change during the observation period, the overall component volume of blood will also not change.

At the beginning of the peritoneal dialysis treatment, there will be a certain percentage of red cell volume per blood component volume in the optical zone. By choosing a wavelength of light which is isobestic for the hemoglobin (Hb) contained in the red cells, the light will be absorbed and scattered by the red cell volume. This wavelength may be one selected in between approximately 800 nm through 830 nm. Blood is the only thing moving in the "optical zone" or observation zone area. Tissue, bone, muscle, etc. remain constant once the sensor pad 116 is securely in place.

Additionally, red cell volume in the body does not change with dialysis. However, excess fluids and toxins are removed, causing a reduction in blood volume. This reduction causes the blood to hemo-concentrate with a higher red cell (and, hence, higher Hb) concentration to occur in the component of blood volume being viewed in the "optical zone" with the transcutaneous sensor 116.

The hemo-concentration of the overall body's blood is assumed to eventually propagate out to the capillary beds including those comprising the component blood volume located under the "optical zone" of the sensor 116. Therefore, the Hb level will rise with hemo-concentration in the blood volume component under the sensor in the optical zone. Equation 1 provides the concentration of red blood cell volume as a fraction of the total blood volume.

$$HCT = \frac{RBCV}{TBV} \approx 3Hb \tag{1}$$

where Hb is the hemoglobin (Hb) concentration as a fraction of total blood volume, HCT is the concentration of red blood cell volume as a fraction of total blood volume, RBCV is red blood cell volume which may be estimated as the red blood cell count multiplied by the average red blood cell volume, and TBV is total blood volume.

While the definitions provided in Equation 1 apply to the entire pool of blood in the body, the values can be prorated based on a reduced volume of the sample. This process is used in laboratory tests. As such, blood draws at the lab can accurately portray the status of blood constituents based on a test tube sample size. In a similar manner, the optical zone viewed by the sensor 116 is seen as a surrogate for a test tube. Therefore, Equation 1 may be re-defined as:

$$HCT = \frac{RBV}{TSV} \approx 3Hb \quad (2)$$

where Hb is the hemoglobin (Hb) concentration as a fraction of sample blood volume, HCT is the concentration of red blood cell volume as a fraction of sample blood volume, RBV is red blood cell volume in the sample of blood which may be estimated as the red blood cell count in the sample multiplied by the average red blood cell volume, and TSV is total sample volume.

Since the constituent of interest here is to determine the percentage change in blood volume using Hb or HCT as an indicator, Equation 2 is solved for TSV to obtain Equation 3.

$$TSV = \frac{RBV}{HCT} \approx \frac{RBV}{3Hb} \quad (3)$$

The percentage change in blood volume in the overall patient's body (shown in Equation 4) is described by as percentage change in TSV over a duration of time between an initial time t=0 and a measurement time t equals m.

$$\%\Delta BV = \frac{TSV_m - TSV_0}{TSV_0} \quad (4)$$

where % ΔBV is the percentage change in blood volume, $TSV_o$ is an initial value of the sample volume, and $TSV_m$ is a value of the sample volume during measurement at a time m. Substituting Equation 3 into Equation 4 and solving for Hb provides Equation 5.

$$\%\Delta BV = \frac{Hb_0 - Hb_m}{Hb_m} \quad (5)$$

where $Hb_o$ is an initial concentration of Hb, and $Hb_m$ is a concentration of Hb during measurement at a time m.

Now consider the "optical zone" of the sensor 116. Within the optical zone is a finite total amount of blood volume (OV) contained within the emitter 304. The size of the optical zone is constant for a given patient as long as the sensor 116 is secure. However, the volume of blood illuminated is likely to change from patient to patient. As such, this volume is unknown. Based on Beers Law, the sensor 116 registers a voltage measurement relative to the amount of Hb present in the unknown optically illuminated blood volume OV. Hb is proportional to the volume of red cells present in this volume because red cells contain the Hb substance.

At 810 nm, the Hb relative concentration in the illuminated blood volume OV is obtained through solving Beer's Law:

$$i_0 = I_0 e^{-\varepsilon Xd} \quad (6)$$

where $i_0$ is the light intensity received at the photodetector at the start of measurement, $I_o$ is light intensity transmitted into the tissue by the LED, e is the exponential term, ε represents the extinction coefficient (includes absorption of the light the material under test), X represents the molar concentration (moles/liter) of Hb in volume OV, and d is the distance between the photodetector and the LED. Note that d is constant after securely placing sensor pad 116. Solving for $X_o$ at time zero provides Equation 7:

$$X_0 = \frac{-\ln\left(\frac{i_o}{I_o}\right)}{\varepsilon d} = \frac{Hb_0}{OV} \quad (7)$$

Solving for $X_m$ at any measurement time after time zero provides Equation 8, where $i_m$ is the intensity of the, for example, 810 nm signal during measurement after time=0:

$$X_m = \frac{-\ln\left(\frac{i_m}{I_o}\right)}{\varepsilon d} = \frac{Hb_m}{OV} \quad (8)$$

Solving for $Hb_o$ and $Hb_m$ yields Equations 9 and 10:

$$Hb_o = X_o \times OV \quad (9)$$

$$Hb_m = X_m \times OV \quad (10)$$

Substituting Equations 9 and 10 into Equation 5 yields Equation 11:

$$\%\Delta BV = \frac{XoOV - XmOV}{XmOV} = \frac{Xo - Xm}{Xm} \quad (11)$$

Substituting in Equations 7 and 8 into Equation 11, and reducing yields Equation 12:

$$\%\Delta BV = \frac{\ln\left(\frac{i_o}{I_o}\right)}{\ln\left(\frac{i_m}{I_o}\right)} - 1 \quad (12)$$

Through algebraic manipulation, Equation 12 may be written as the natural log of the ratio of $i_o$ and $I_o$ divided by the natural log of the ratio of $i_m$ and $I_o$.

From Equation 12, all that is required in this measurement of change in blood volume application is an initial calibration of the light transmitted into the tissue $I_o$. The preferred method is completed using a synthetic block of sufficient depth to accommodate inclusion of the optical zone volume and made of opaque material, such as silicon, having a known extinction coefficient at the selected wavelength between 800 nm to 830 nm. Calibration is accomplished by placing the sensor's optical zone against the block and adjusting $I_o$ for predetermined received i value. In some embodiments, prior to measurement, a reconfigurable sensor 116 may allow for adjustment of the distance d between the LED and photodetector. In this embodiment, the light transmitted into the tissue $I_o$ is a preconfigured value, and the distance d between the LED and photodetector is selected to illuminate a sufficient volume of tissue to meet adequate signal-to-noise considerations and other measurement margins while detecting Hb. In some cases, such as on the arm or leg, the placement of the optical sensor may be on a curved surface causing the planar geometry of the sensor to be compromised. This is of little consequence so long as the distance d is sufficient to illuminate a fixed amount of skin and tissue containing a blood supply and the placement is fixed without movement.

Also, because $I_o$ is a fixed value during the measurement period, it may be somewhat arbitrary because its value governs the amount of blood volume in the "optical zone" that is illuminated. The higher $I_o$, the more volume is illuminated and as a result, i.e., more capillaries of blood will be illuminated. As more volume of blood is illuminated, the more Hb will be proportionally sensed. If $I_o$ becomes too high, the optical zone can exceed the boundaries of collateral or depth of the skin and tissue resulting in compromised results. As such, $I_o$ should not exceed a value that causes the optical zone to extend beyond the boundaries of the material under test. The preferred method of $I_o$ adjustment is through use of the silicon calibration block. Due to variation in patient physiology, the proration of blood in the illuminated zone is likely to vary. As with the test tube example, regardless of the sample size, the ratio of red cell volume (hence Hb) will be a constant when taken against the sample volume.

In FIG. 3, the BV measurement system 308 may store at memory 320 the initial calibration value representing $I_o$ for a given LED and photodetector distance. This value representing $I_o$ may be programmed and changed through controller 310 for different LED and photodetector distances, for different LED wavelengths, and for the sensitivity of the photodetector. In some embodiments, the value representing $I_o$ is a current provided to the LED, and the controller 310 obtains this value from memory 320 and generates a transmitter control signal 309 to control the LED current source 305.

At the beginning of measurement, the photodetector 306 receives $i_o$ and generates an electrical signal that is provided to the BV measurement system 308. During measurement, the photodetector 306 continues to generate different light intensity $i_m$ as the treatment progresses and provides electrical signals to the BV measurement system 308. The electrical signals provided are proportional to the magnitude of the different $i_m$ readings. The BV measurement system 308 may then store at the memory 320 an initial calibration value $I_o$ of the light intensity transmitted into the tissue by the emitter 304, an initial measured value of the light at the photodetector 306 $i_o$, and during treatment receiving measured signals representing measured light $i_m$, and using these three values to determine percentage change in blood volume according to the relationship in Equation 11. Due to the proportional relationship between electrical current and light intensity, current provided to the emitter 304 and current measured from the photodetector 306 represent the different light intensities in Equation 11.

Figure 4A:
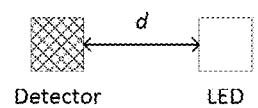
FIGS. 4A-4C show example configurations of photodetectors and LEDs according to some embodiments of the disclosure.
Figure 4B:
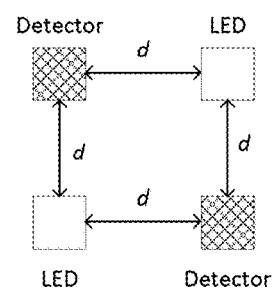
Figure 4C:
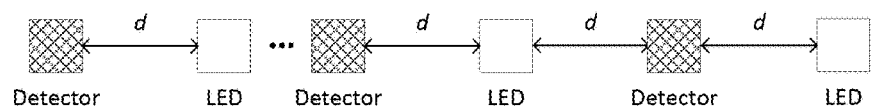

As previously mentioned, configurations of the sensor 116 other than those illustrated in FIGS. 1 and 2 may be used. FIGS. 4A-4C illustrate example embodiments of configurations for the emitter 304 and photodetector 306 that may be used instead of or in addition to the configuration illustrated in FIG. 2. The configurations in FIGS. 4A-4C provide a top view of emitters 304 and photodetectors 306 placed on a surface. FIG. 4A illustrates a configuration where only one emitter 304 and one photodetector 306 comprise the sensor 116. FIG. 4B is a top view of emitters 304 and photodetectors 306 illustrating a configuration where two emitters 304 and two photodetectors 306 are positioned in four corners of a square to comprise the sensor 116. FIG. 4C illustrates a configuration similar to FIG. 2, but the pattern of FIG. 4C is repeated for a greater number of "optical zones." In the configurations of FIGS. 4A-4C, distance d is provided as an example, but all configurations need not have the same distance d, since all channels are independent and have separate calibration. The resulting values of percent change in blood volume from each channel may be averaged for a composite value for storage and display or may be stored and displayed separately. Stored data can be downloaded later for additional analysis.

When the sensor 116 includes more than one pair of emitter 304 and photodetector 306, the change in blood volume may be determined to be an average of the change calculated for each optical zone corresponding to each emitter/photodetector pair as illustrated in FIG. 2. In some embodiments, a median value from all the calculated values in each optical zone is selected as the change in blood volume. By having values for more than one optical zone, other statistical methods, for example, root mean square, may be applied to determine change in blood volume from the values obtained from the system in FIGS. 3 and 3A. In embodiments with more than one "optical zone" (for example, in FIG. 2), the measurements are performed one "optical zone" at a time, eliminating light interference between LED1 and LED2.

Figure 5:
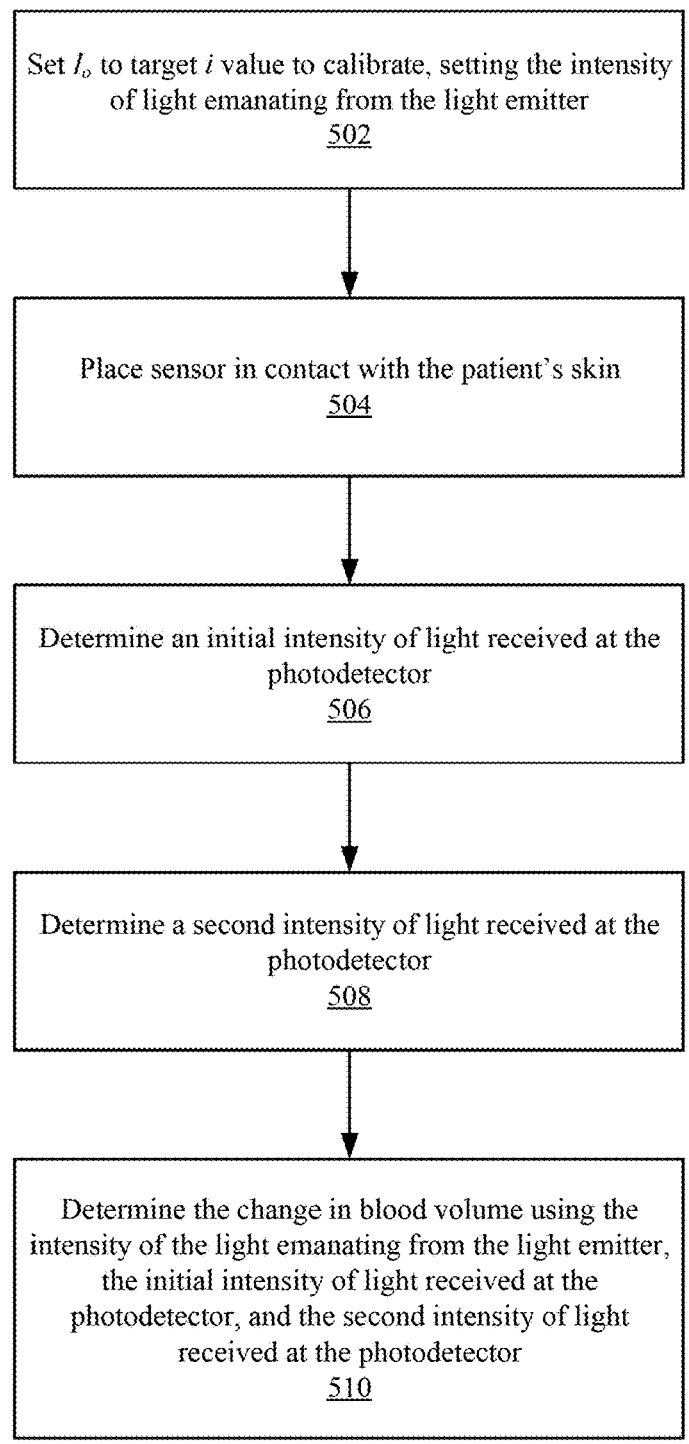
FIG. 5 illustrates a process of determining change in blood volume according to some embodiments of the disclosure.

A process of making measurements according to an embodiment of the disclosure is illustrated as a flow diagram in FIG. 5. Prior to measurement during peritoneal dialysis, at step 502, the sensor is placed on the silicon calibration block, and $I_o$ is adjusted to adjust the predetermined value of i. Once $I_o$ is acceptable, for calculation purposes, this $I_o$ is used as the intensity of light emanating from the light emitter. At step 504, a sensor 116, including at least one emitter/photodetector pair, is placed in contact with the skin of the patient 102. The emitter/photodetector pair may be configured as in one of the illustrated embodiments or other configurations as long as the configuration includes one or more photodetectors with one or more emitters separated by a spacing, electronic drivers to provide power to the one or more emitters, and a controller that allows setting the current or power provided to the one or more emitters and is able to receive electrical signals generated from the one or more photodetectors. Step 504 involves securing the sensor 116 to the skin of the patient 102 to avoid the sensor moving during the measurement process. In all cases, the sensor pad must be firmly placed against the skin to establish optical coupling between emitters and detectors with the skin. This is often aided by placing the sensor on an appendage such as the arm and using medical wrapping material to secure the sensor without being so tight as to cut off circulation. The devices must be firmly in contact with the skin for best optical coupling. Because the intensity of the emitter 304 is directly proportional to the current flowing through the emitter, the current provided by the power supply 302 may be used by the BV measurement system 308 as a representation of the light intensity of the emitter. Though calibrated in step 502, the current can be monitored for variation and in one embodiment could use controller 310 to monitor and manage this current through the transmitter control 309. In other instances, the current may be combined with a sensed voltage across the emitter 304 to determine power consumption of the emitter 304. The power consumption of the emitter 304 may be used by the BV measurement system 308 as a representation of the light intensity $I_o$ of the emitter. In another embodiment, this power level could be used to compensate the emitter 304 by the controller 310 through the transmitter control 309.

At step 506, the initial intensity $i_o$ of light received at the photodetector 306 is determined. This process involves measuring a current produced by the photodetector 306. For example, the trans-impedance amplifier 331 senses the current generated at the photodetector 306 in response to the emitter's illumination. Step 506 involves noting the initial intensity $I_o$ through the current sensed from the photodetector 306 at time zero when the peritoneal dialysis treatment begins. At step 508, the process involves determining a second intensity of light $i_m$ received at the photodetector 306. This step is similar to that of step 506 and made at times greater than zero as the peritoneal dialysis treatment progresses. Because of the time delay in central blood moving to the capillary locations, there may be further changes in this measurement after peritoneal dialysis treatment has ceased. Leaving this system active for a period of time (for example, half an hour) after the peritoneal dialysis treatment will allow for a more accurate final blood volume change measurement.

At step 510, the change in blood volume is determined using the initial intensity of light emanating from the light emitter 304, the initial intensity of light received at the photodetector 306, and the second intensity of light received at the photodetector. Using the relationship in Equation 11, the measured values of these different components are combined to estimate the change in blood volume.

Various embodiments discussed herein may be combined with each other in appropriate combinations in connection with the system described herein. Additionally, in some instances, the order of steps in the flowcharts, flow diagrams and/or described flow processing may be modified, where appropriate. Further, various aspects of the system described herein may be implemented using software, hardware, a combination of software and hardware and/or other computer-implemented modules or devices having the described features and performing the described functions.

Software implementations of aspects of the system described herein may include executable code that is stored in a computer readable medium and executed by one or more processors. The computer readable medium may include volatile memory and/or non-volatile memory, and may include, for example, a computer hard drive, ROM, RAM, flash memory, portable computer storage media such as a CD-ROM, a DVD-ROM, a flash drive and/or other drive with, for example, a universal serial bus (USB) interface, and/or any other appropriate tangible or non-transitory computer readable medium or computer memory on which executable code may be stored and executed by a processor. The system described herein may be used in connection with any appropriate operating system.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for measuring change in blood volume using a sensor comprising a light emitter and a photodetector in contact with a tissue membrane of a patient, the method comprising:
setting an intensity of light emanating from the light emitter and through an optical zone of the tissue;
determining an initial intensity of the light received at the photodetector after passing through the optical zone;
determining a second intensity of the light received at the photodetector after passing through the optical zone, wherein the second intensity is determined at a predetermined time after the determination of the initial intensity; and
determining a change in blood volume of the patient based on the intensity of the light emanating from the light emitter, the initial intensity of light received at the photodetector, and the second intensity of light received at the photodetector by determining:
a first ratio as a ratio between the initial intensity of light received at the photodetector and the intensity of light emanating from the light emitter,
a second ratio as a ratio between the second intensity of light received at the photodetector and the intensity of light emanating from the light emitter, and
that the change in blood volume is proportional to a natural log of the first ratio divided by a natural log of the second ratio.

2. The method according to claim 1, wherein the light emitter is a light emitting diode (LED) and the photodetector is a photodiode.

3. The method according to claim 2, wherein the LED is positioned at a spacing (d) from the photodetector, and wherein d is such that the photodetector is within the optical zone of the LED.

4. The method according to claim 2, wherein the LED emits light at an isosbestic wavelength that is scattered and absorbed by hemoglobin and unaffected by oxygen variation.

5. The method according to claim 2, wherein the setting an intensity of light emanating from the light emitter is:
providing an electrical current at a predetermined current level to the LED, or
providing an electrical power a predetermined power level to the LED.

6. The method according to claim 2, wherein the determining an initial intensity of light received at the photodetector comprises:
receiving an electrical current from the photodiode, the electrical current being proportional to a light intensity sensed by the photodiode.

7. The method of claim 1 further comprising:
sending data containing the change in blood volume to a peripheral device, wherein the peripheral device is configured to send the data through a network connection to a remote server.

8. The method of claim 1, wherein the patient is a dialysis patient and the sensor is placed on the patient's arm or leg.

9. A system for measuring change in blood volume comprising:
a sensor comprising at least one emitter and at least one photodetector in contact with a tissue membrane of a patient;
a controller, coupled to the sensor; and
a power supply coupled to both the sensor and the controller, wherein:
the power supply is configured to provide an electrical power to the at least one emitter in the sensor,
the at least one photodetector is configured to provide to the controller (a) a second set of signals indicative of light intensities received at the at least one photodetector due to a first set of signals and (b) a third set of signals indicative of light intensities received at the at least one photodetector due to the first set of signals at a predetermined time after providing the second set of signals, and
the controller is configured to (c) provide to the power supply the first set of signals indicating intensities of light emanating from the at least one emitter, where a number of signals in the first set of signals matches a number of emitters in the at least one emitter, and
(d) determine a change in blood volume from the first, second and third sets of signals by:
dividing numbers in the second set of signals by numbers in the first set of signals to determine a first set of ratios,
dividing numbers in the third set of signals by numbers in the first set of signals to determine a second set of ratios,
dividing a natural log of the first set of ratios by a natural log of the second set of ratios to determine an intermediate set, and
determining the change in blood volume as a function of values in the intermediate set.

10. The system of claim 9, wherein the controller determines that the change in blood volume is a median of the values in the intermediate set.

11. The system of claim 9, wherein the controller determines that the change in blood volume is an average of the values in the intermediate set.

12. The system of claim 9, wherein each emitter in the at least one emitter is positioned at a spacing d from a photodetector of the at least one photodetector, and wherein d is such that the photodetector is within the optical zone of said each emitter.

13. The system of claim 9, wherein the controller is coupled to the sensor through one or more trans-impedance amplifiers and one or more analog to digital converters (ADC), and wherein the trans-impedance amplifiers convert electrical current from the at least one photodetector to electrical voltage and the ADCs convert the electrical voltage to a digital signal input to the controller.

14. The system of claim 9, wherein the at least one emitter emits light at an isosbestic wavelength that is scattered and absorbed by hemoglobin and unaffected by oxygen variation.

15. The system of claim 9, wherein each emitter in the at least one emitter is turned on one emitter at a time so that each photodetector in the at least one photodetector obtains the second set of signals and the third set of signals one signal at a time.

16. The system of claim 9, further comprising:
a transmitter, configured to send the change in blood volume to a peripheral device for transmission through a network connection to a remote server.

17. A non-transient computer readable medium containing program instructions for causing a controller coupled to a sensor comprising a light emitter and a photodetector in contact with a tissue membrane of a patient to perform the method of:
setting an intensity of light emanating from the light emitter and through an optical zone of the tissue;
determining an initial intensity of the light received at the photodetector after passing through the optical zone;
determining a second intensity of the light received at the photodetector after passing through the optical zone, wherein the second intensity is determined at a predetermined time after the determination of the initial intensity; and
determining a change in blood volume of the patient based on the intensity of the light emanating from the light emitter, the initial intensity of light received at the photodetector, and the second intensity of light received at the photodetector by determining:
a first ratio as a ratio between the initial intensity of light received at the photodetector and the intensity of light emanating from the light emitter,
a second ratio as a ratio between the second intensity of light received at the photodetector and the intensity of light emanating from the light emitter, and
that the change in blood volume is proportional to a natural log of the first ratio divided by a natural log of the second ratio.

18. The non-transient computer readable medium according to claim 17, wherein the light emitter is a light emitting diode (LED) and the photodetector is a photodiode.

19. The non-transient computer readable medium according to claim 18, wherein the determining an initial intensity of light received at the photodetector comprises:

receiving an electrical current from the photodiode, the electrical current being proportional to a light intensity sensed by the photodiode.

* * * * *